(12) United States Patent
Hyman (10) Patent No.: US 6,959,814 B1
(45) Date of Patent: Nov. 1, 2005

(54) PORTABLE INSULIN CADDY

(76) Inventor: Jane M Hyman, 312 Garfield Ave., Steubenville, OH (US) 43952

( * ) Notice: Subject to any disclaimer, the term of this patent is extended or adjusted under 35 U.S.C. 154(b) by 0 days.

(21) Appl. No.: 10/735,683

(22) Filed: Dec. 15, 2003

(51) Int. Cl.[7] ............................................. B65D 71/00
(52) U.S. Cl. ...................... 206/570; 206/366; 206/545; 206/571; 206/826; D24/130; D3/204.8; 62/372; 62/457.2
(58) Field of Search ................................ 206/570, 366, 206/545, 571, 826, 823, 364, 363; 62/372, 62/457.2; D24/130; D3/203.8, 299

(56) References Cited

U.S. PATENT DOCUMENTS

| | | | | |
|---|---|---|---|---|
| 4,429,793 A | * | 2/1984 | Ehmann | ...................... 206/570 |
| 4,657,138 A | * | 4/1987 | Watson | ...................... 206/366 |
| D338,781 S | * | 8/1993 | Eitel | ........................ D3/203.8 |
| 6,439,276 B1 | * | 8/2002 | Wood et al. | .................. 141/97 |
| D473,715 S | * | 4/2003 | Moldovan | .................... D3/299 |
| 6,605,065 B1 | * | 8/2003 | Tarentino | ..................... 604/187 |

FOREIGN PATENT DOCUMENTS

| | | | | |
|---|---|---|---|---|
| EP | 397607 A | * | 11/1990 | ............. A61J 1/16 |
| GB | 2237204 A | * | 5/1991 | ............. A61J 1/16 |

* cited by examiner

Primary Examiner—Jila M. Mohandesi
(74) Attorney, Agent, or Firm—Michael I Kroll (57) ABSTRACT

The present invention 10 is a portable insulin and accessory kit for diabetics that is a case 24 made of polymeric or waterproof material having an inside portion divided in three equal sections, each section securing and storing insulin and accessories such as an insulin pen or syringe 26, alcohol cloths 16 or similar accessories for sterilization and a supply of additional needles 18. The kit is foldable and provides hook and loop fasteners 20 for a secure closure. In addition, a polymeric, portable insulin storage box 28 is provided having a hingedly attached cover 32 attached to a bottom portion having divided sections for the storage of insulin and accessories such as an insulin pen or syringe 26, alcohol cloths 16 or similar accessories for sterilization and a supply of additional needles 34.

6 Claims, 9 Drawing Sheets

PORTABLE INSULIN CADDY

BACKGROUND OF THE INVENTION

1. Field of the Invention

The present invention relates generally to portable insulin storage and, more specifically, to a portable insulin and accessory kit for diabetics that is comprised of a polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable and provides hook and loop fasteners for a secure closure. The diabetic insulin kit of the present invention provides a compact, sanitary means for travel.

In addition, a polymeric, portable insulin storage box is provided comprising a hingedly attached cover to a bottom portion having divided sections for the storage of insulin and accessories such as an insulin pen or syringe, alcohol cloths or similar accessories for sterilization and a supply of additional needles.

2. Description of the Prior Art

There are other insulin storage devices designed for the purpose of the present invention.

While these devices may be suitable for the purposes for which they were designed, they would not be as suitable for the purposes of the present invention as heretofore described.

It is thus desirable to provide a portable insulin and accessory kit for diabetics that is comprised of a polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable and provides hook and loop fasteners for a secure closure. The diabetic insulin kit of the present invention provides a compact, sanitary means for travel.

In addition, a polymeric, portable insulin storage box is provided comprising a hingedly attached cover to a bottom portion having divided sections for the storage of insulin and accessories such as an insulin pen or syringe, alcohol cloths or similar accessories for sterilization and a supply of additional needles.

SUMMARY OF THE PRESENT INVENTION

The present invention discloses a portable insulin and accessory kit for diabetics that is comprised of a case made of polymeric or waterproof material having an inside portion divided in three equal sections, each section providing means for securing and storing insulin and accessories such as an insulin pen or syringe, alcohol cloths or similar accessories for sterilization and a supply of additional needles. The kit is foldable and provides hook and loop fasteners for a secure closure. In addition, a polymeric, portable insulin storage box is provided comprising a hingedly attached cover attached to a bottom portion having divided sections for the storage of insulin and accessories such as an insulin pen or syringe, alcohol cloths or similar accessories for sterilization and a supply of additional needles.

A primary object of the present invention is to provide a portable insulin and accessory kit for diabetics.

Another object of the present invention is to provide a portable insulin and accessory kit for diabetics that is comprised of a polymeric or water proof material.

Yet another object of the present invention is to provide a portable insulin and accessory kit for diabetics that the inside portion is divided in three equal sections, each section providing means for the securing and storing of insulin and accessories.

Still yet another object of the present invention is to provide a portable insulin and accessory kit for diabetics that an inside portion divided in three equal sections, each section providing means for the securing and storing of insulin and accessories such as an insulin pen or syringe, alcohol cloths or similar accessories for sterilization and a supply of additional needles.

Another object of the present invention is to provide a portable insulin and accessory kit for diabetics that is foldable and provides hook and loop fasteners for a secure closure.

Yet another object of the present invention is to provide a portable insulin and accessory kit for diabetics that provides a compact, sanitary means for travel.

Still yet another object of the present invention is to provide a portable insulin and accessory kit for diabetics that in addition, a polymeric, portable insulin storage box is provided comprising a hingedly attached cover to a bottom portion having divided sections for the storage of insulin and accessories such as an insulin pen or syringe, alcohol cloths or similar accessories for sterilization and a supply of additional needles.

Additional objects of the present invention will appear as the description proceeds.

The present invention overcomes the shortcomings of the prior art by providing a portable insulin and accessory kit for diabetics that is comprised of a polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable and provides hook and loop fasteners for a secure closure. The diabetic insulin kit of the present invention provides a compact, sanitary means for travel.

In addition, a polymeric, portable insulin storage box is provided comprising a hingedly attached cover to a bottom portion having divided sections for the storage of insulin and accessories such as an insulin pen or syringe, alcohol cloths or similar accessories for sterilization and a supply of additional needles.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

With regard to reference numerals used, the following numbering is used throughout the drawings.

10 present invention
12 user
14 elastic fastener
16 alcohol pads
18 storage for additional needles
20 hook and loop fasteners
22 clear plastic pocket
24 case
26 syringe
28 box
30 hinge
32 cover
34 needles

DETAILED DESCRIPTION OF THE PREFERRED EMBODIMENT

The following discussion describes in detail one embodiment of the invention. This discussion should not be construed, however, as limiting the invention to those particular embodiments since practitioners skilled in the art will recognize numerous other embodiments as well. For a definition of the complete scope of the invention, the reader is directed to the appended claims.

Figure 1:
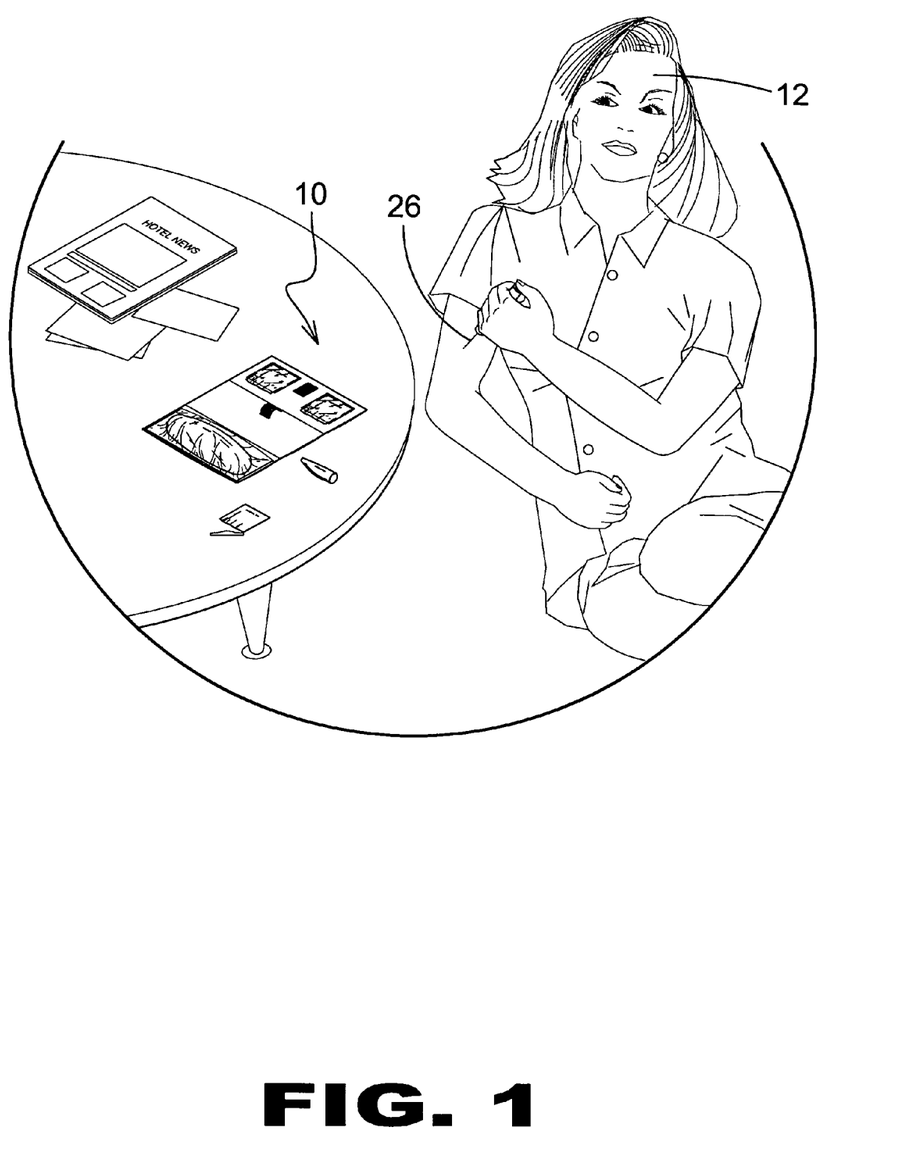
FIG. 1 is an illustrative view of the present invention, an insulin caddy, in use.

Turning to FIG. 1, shown therein is an illustrative view of the present invention 10 in use by a user 12. The present invention 10 is a portable insulin and accessory kit for diabetics 12 that is comprised of a polymeric or water proof material having an inside portion divided in three equal sections, each section providing means for securing and storing insulin and accessories such as an insulin pen or syringe 26, alcohol cloths or similar accessories for sterilization and a supply of additional needles. The kit 10 is foldable and provides hook and loop fasteners for a secure closure. The diabetic insulin kit of the present invention 10 provides a compact, sanitary means for travel.

Figure 2:
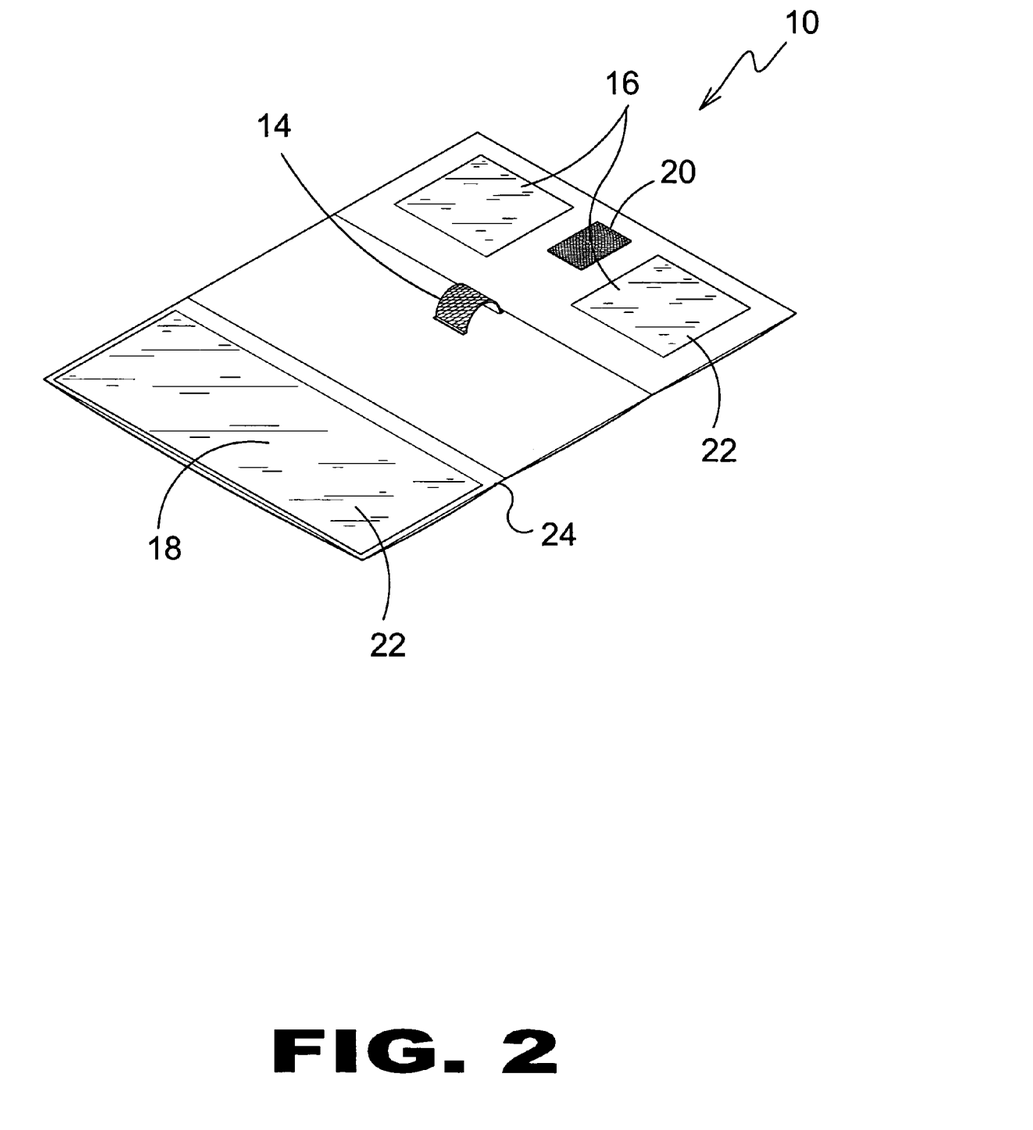
FIG. 2 is a perspective view of the present invention, an insulin caddy.

Turning to FIG. 2, shown therein is a perspective view of the present invention 10. Shown is the present invention 10 being a portable insulin and accessory kit for diabetics that is comprised of a planar, rectangular case 24 made of polymeric or water proof material having an inside portion divided in three equal sections, each section providing means for the securing and storing of insulin and accessories such as an insulin pen or syringe 14, alcohol cloths 16 or similar accessories for sterilization and a supply of additional needles 18. The kit 10 is foldable and provides hook and loop fasteners 20 for a secure closure. Clear plastic pocket areas 22 are also shown.

Figure 3:
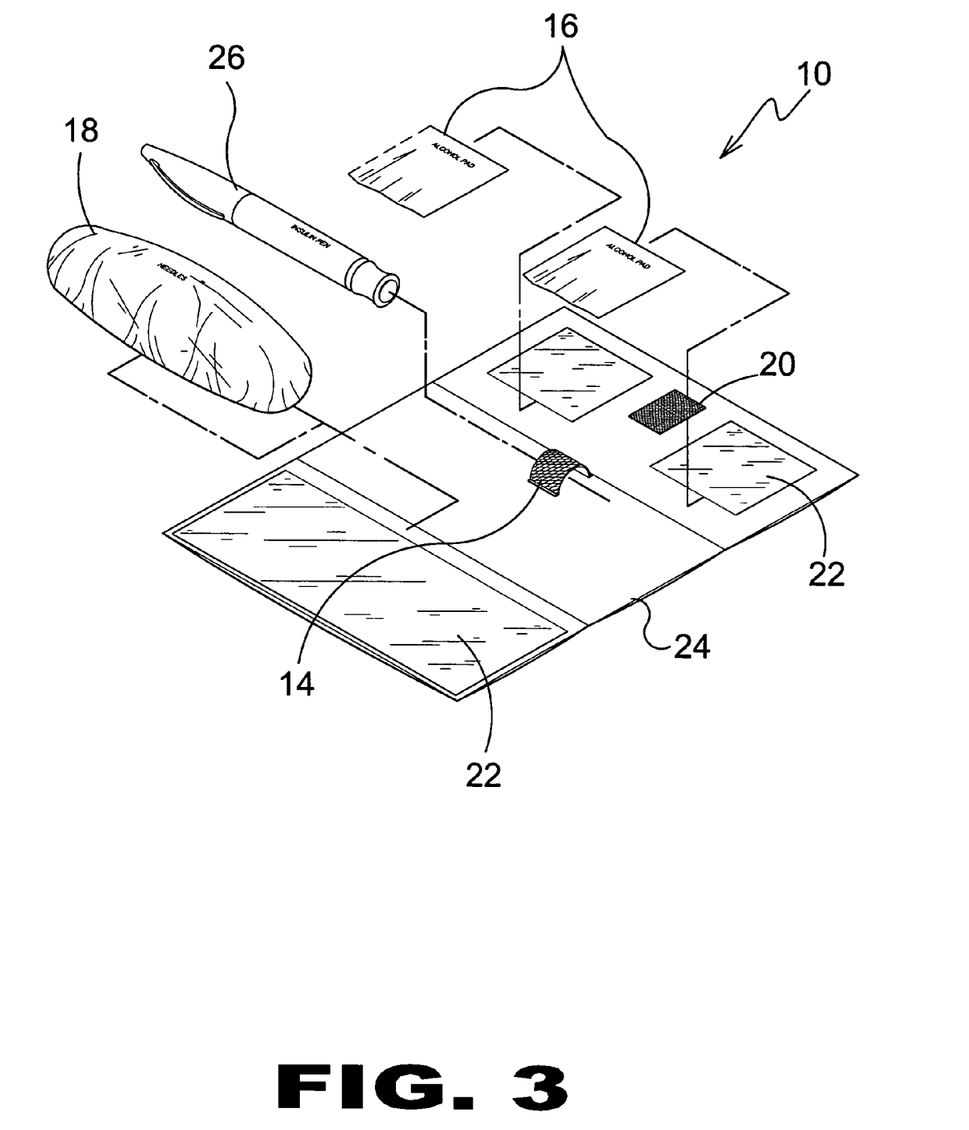
FIG. 3 is an exploded view of the present invention, an insulin caddy.

Turning to FIG. 3, shown therein is an exploded view of the present invention 10. Shown is the present invention 10 being a portable insulin and accessory kit for diabetics that is comprised of a polymeric or water proof material case 24 having an inside portion divided in three equal sections, each section providing means for the securing and storing of insulin and accessories such as an insulin pen or syringe 26 disposed in elastomeric fastener 14, alcohol cloths 16 or similar accessories for sterilization and a supply of additional needles 18. The kit is foldable and provides hook and loop fasteners 20 for a secure closure. Clear plastic pocket areas 22 are also shown.

Figure 4:
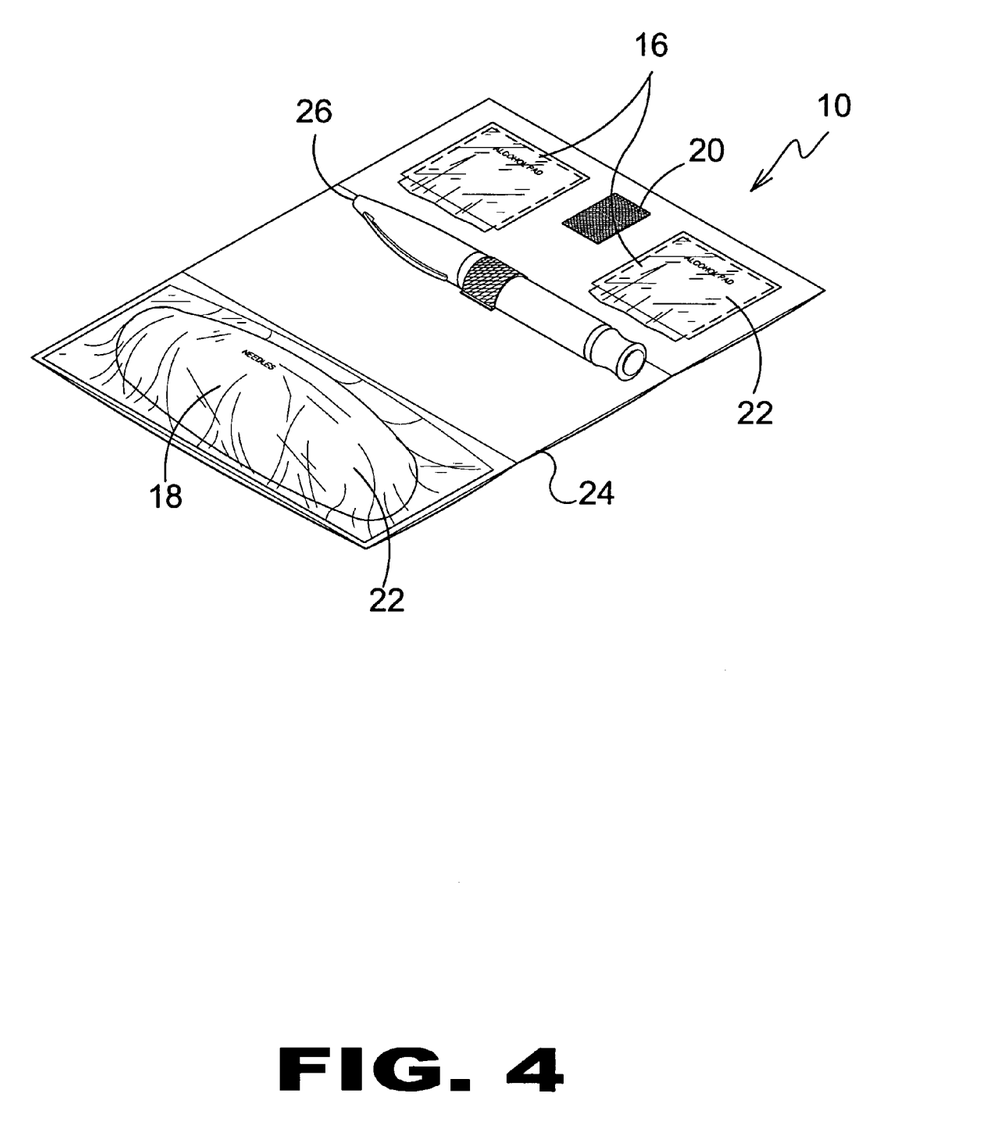
FIG. 4 is a perspective view of an equipped insulin kit of the present invention.

Turning to FIG. 4, shown therein is a perspective view of an equipped insulin kit of the present invention 10. Shown is the present invention 10 being a portable insulin and accessory kit for diabetics that is comprised of a case 24 made of polymeric or water proof material having an inside portion divided in three equal sections, each section providing means for the securing and storing of insulin and accessories such as an insulin pen or syringe 26, alcohol cloths 16 or similar accessories for sterilization and a supply of additional needles 18. The kit is foldable and provides hook and loop fasteners 20 for a secure closure. Clear plastic pocket areas 22 are also shown.

Figure 5:
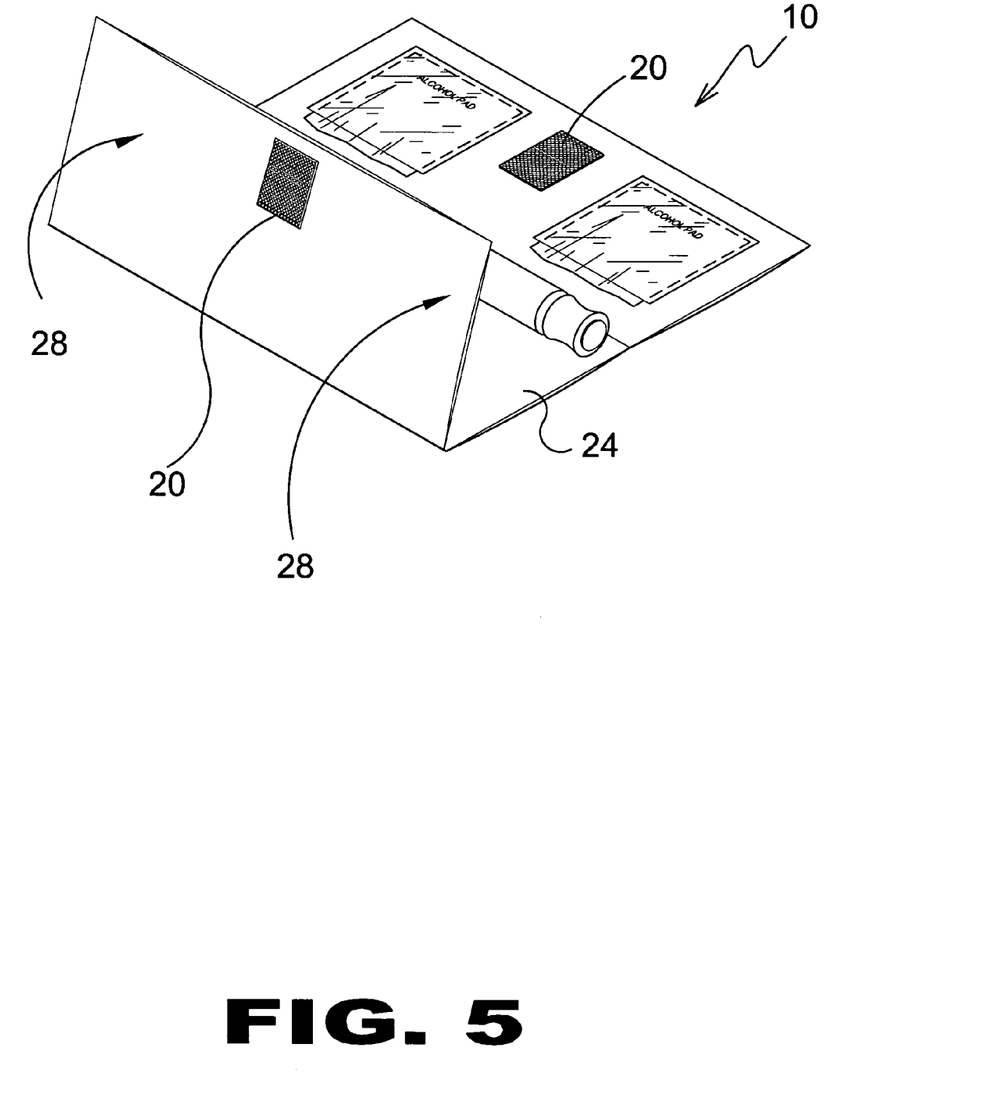
FIG. 5 is a perspective view of the first step in closing the insulin accessory kit of the present invention.

Turning to FIG. 5, shown therein is a perspective view of the first step in closing the insulin accessory kit of the present invention 10. Shown is the present invention 10 being a portable insulin and accessory kit for diabetics that is comprised of a case 24 made of polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable as shown by arrows 28 and provides mating hook and loop fasteners 20 for a secure closure.

Figure 6:
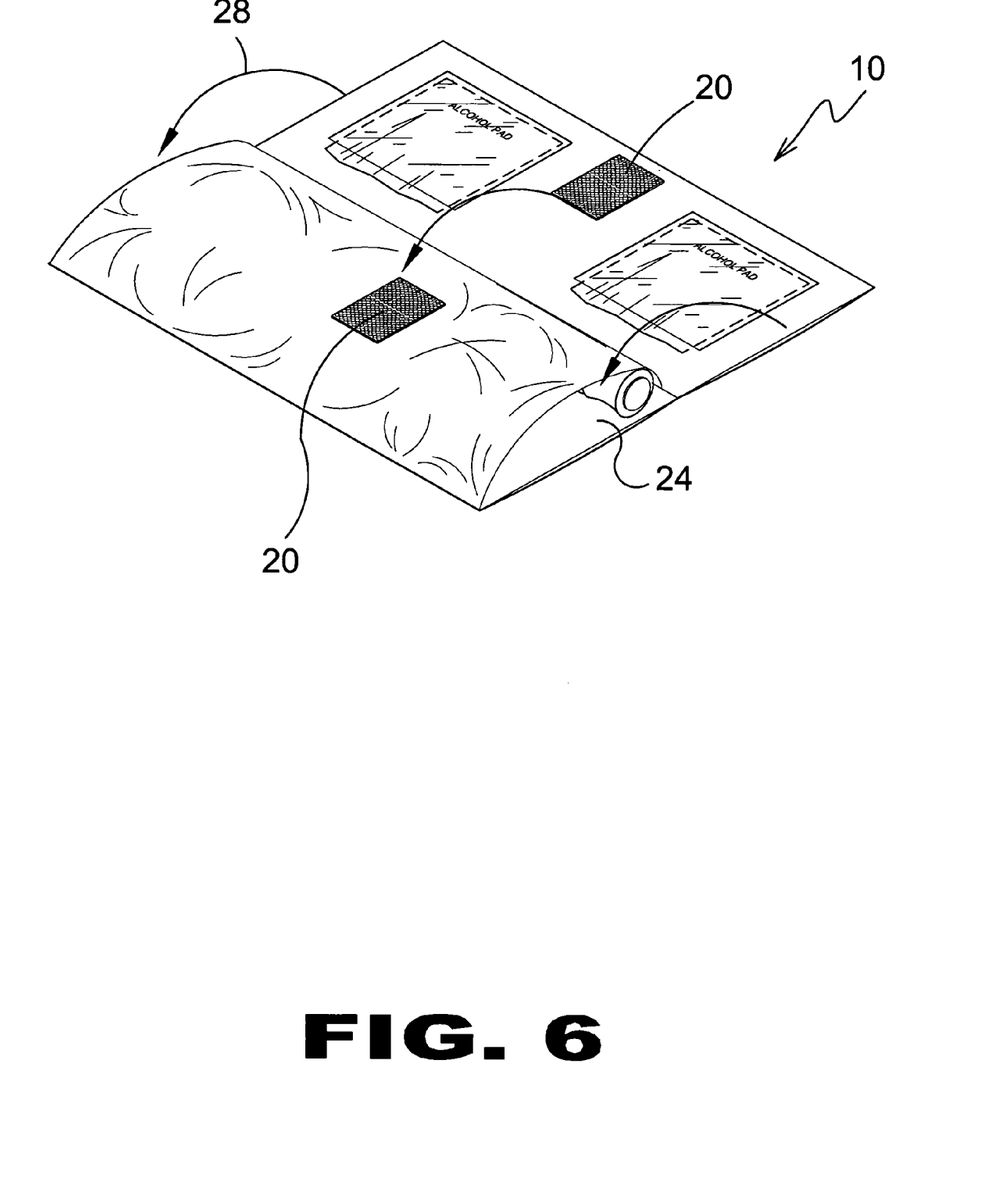
FIG. 6 is a perspective view of the second step in closing the insulin accessory kit of the present invention.

Turning to FIG. 6, shown therein is a perspective view of the second step in closing the insulin accessory kit of the present invention 10. Shown is the present invention 10 being a portable insulin and accessory kit for diabetics that is comprised of a case 24 made of polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable as shown by arrows 28 and provides mating hook and loop fasteners 20 for a secure closure.

Figure 7:
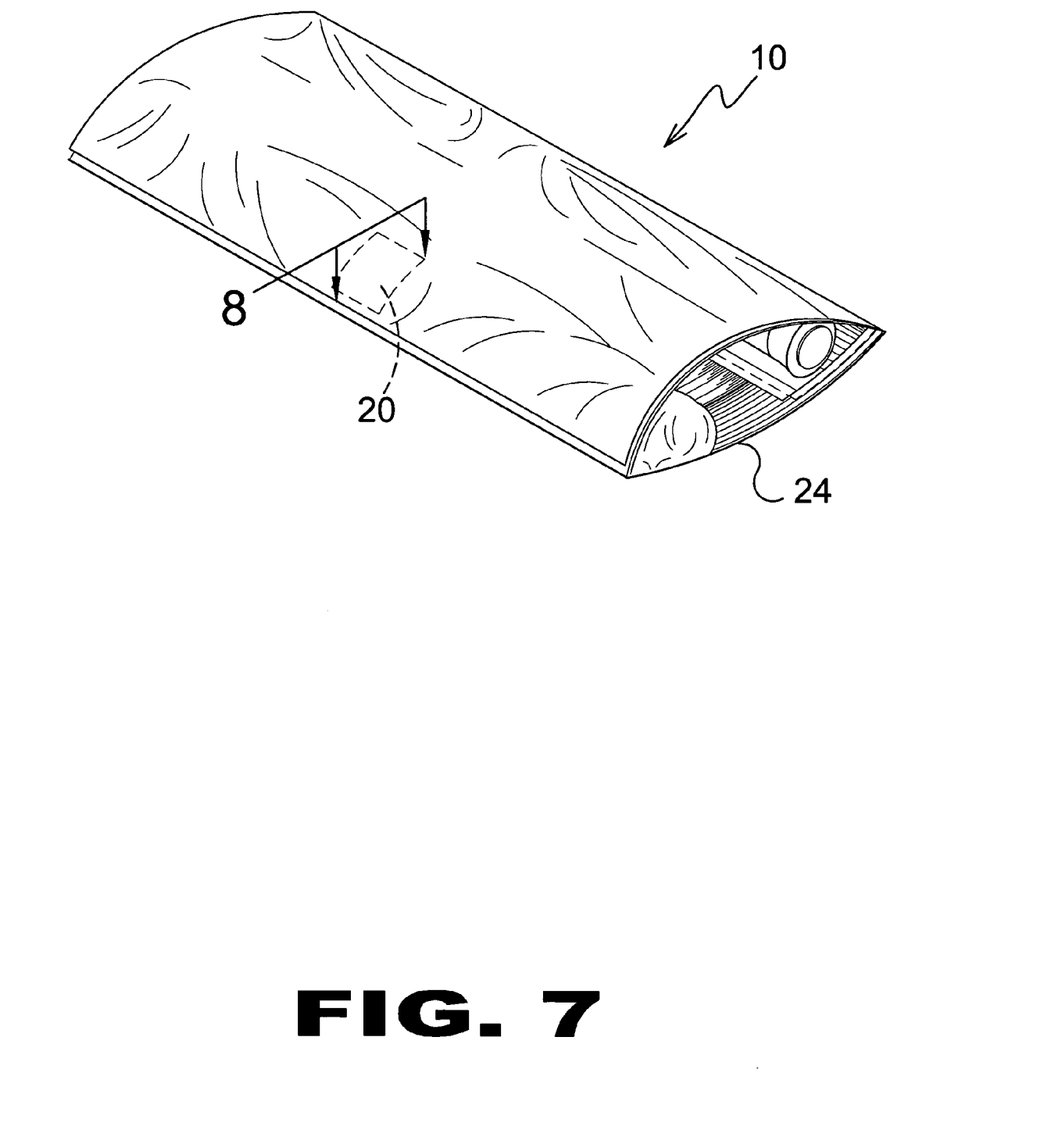
FIG. 7 is a perspective view of the folded insulin accessory kit of the present invention.

Turning to FIG. 7, shown therein is a perspective view of the folded insulin accessory kit of the present invention 10. Shown is the present invention 10 being a portable insulin and accessory kit for diabetics that is comprised of a case 24 made of polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable and provides hook and loop fasteners 20 for a secure closure.

Figure 8:
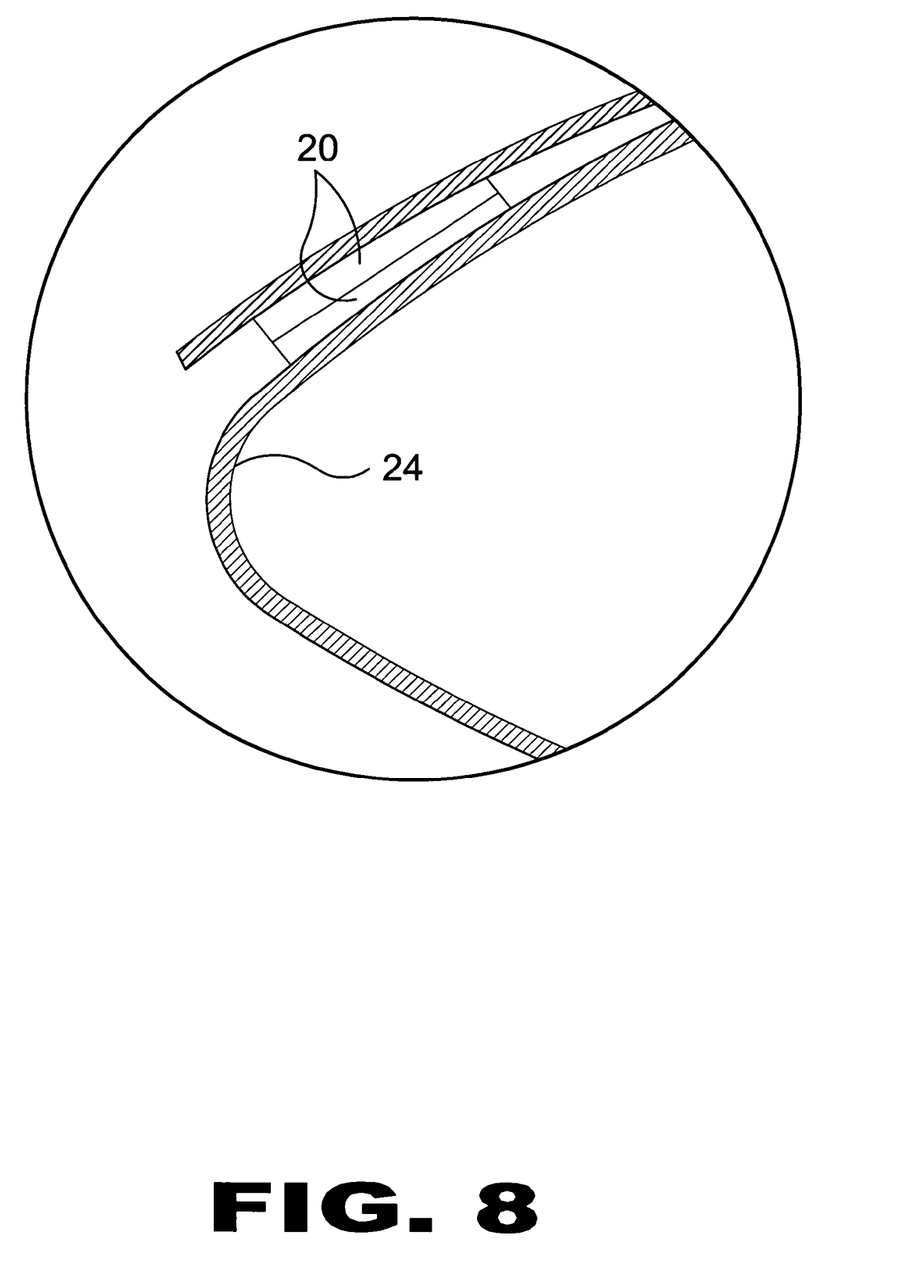
FIG. 8 is a partial sectional view of the folded insulin accessory kit of the present invention.

Turning to FIG. 8, shown therein is a partial sectional view of the folded insulin accessory kit of the present invention. Shown is the present invention being a portable insulin and accessory kit for diabetics that is comprised of a case 24 made of polymeric or water proof material having an inside portion divided in three equal sections, each section providing means for the securing and storing of insulin and accessories such as an insulin pen or syringe, alcohol cloths or similar accessories for sterilization and a supply of additional needles. The kit is foldable and provides mating hook and loop fasteners 20 for a secure closure.

Figure 9:
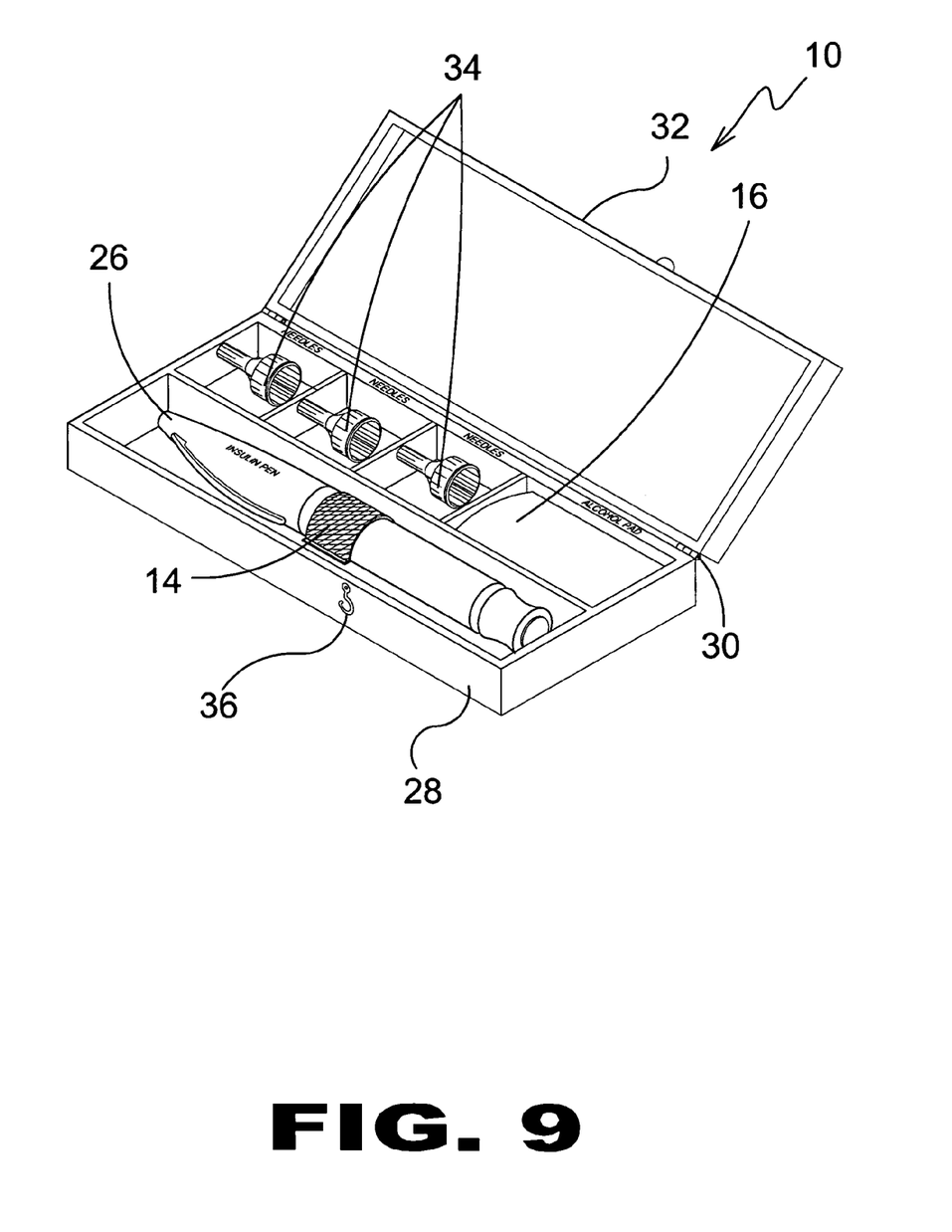
FIG. 9 is a perspective view of an alternate insulin accessory kit of the present invention.

Turning to FIG. 9, shown therein is a perspective view of an alternate insulin accessory kit of the present invention 10. Shown is an alternate of the present invention 10 being a portable insulin and accessory kit for diabetics that is comprised of a polymeric box 28 and hingedly at 30 attached cover 32 having an inside portion divided into sections, each section providing means for the securing and storing of insulin and accessories such as an insulin pen or syringe 26, alcohol cloths 16 or similar accessories for sterilization and a supply of additional needles. In the preferred embodiment, three additional needles 34 and four folded alcohol pads 16 are stored lengthwise within the separate chambers of the polymeric box 28. Also shown are an elastic fastener 14 and a fastener 36 for securing cover 32 in a closed position.

I claim:

1. A portable insulin and accessory kit, consisting of:
   a) a flexible case, said case being substantially rectangular, said case being substantially planar, said case having an opposing first and second end, an opposing first and second side, and an inside and outside;
   b) said case having first, second and third substantially equal sections, wherein said first section is disposed toward said first end, said third section is disposed toward said second end and said second section is disposed between said first and third section, a first fold line between said first and second sections and a second fold line between said second and third sections wherein said third section folds toward said first end over and contiguous to said second sections wherein said first section then folds over said third section so as to position said inside of said third section contiguous to said inside of said second section and said inside of said first section folds contiguous to said outside of said third section;
   c) a clear plastic pocket on the inside of said first section and a pair of clear plastic spaced pockets on the inside of said third section;
   d) a receptacle in the form of a loop on said inside of said second section adjacent said second fold line;
   e) an insulin source in said receptacle;
   f) disinfectant pads in the pockets in said third section;
   g) a plurality of spare needles in the pocket in said first section; and
   h) a hook or loop fastener on the inside of said third section between the pockets therein and a mating hook or loop fastener on the outside of said first section to secure said case in said folded position forming a closed case with opposing convex sides and opposite edges.

2. The kit of claim 1, wherein said case is made of polymeric material to protect the kit.

3. The kit of claim 2, wherein said case is made of waterproof material to protect the kit.

4. The kit of claim 3, wherein said receptacle is made of elastomeric material.

5. The kit of claim 4, wherein said insulin source is a syringe.

6. The kit of claim 4, wherein said insulin source is an insulin pen.

* * * * *